United States Patent
Gu et al.

(10) Patent No.: US 10,849,560 B2
(45) Date of Patent: Dec. 1, 2020

(54) HOST OF PHYSIOLOGICAL DETECTION SYSTEM AND PHYSIOLOGICAL DETECTION DEVICE WITH HIGH ACCURACY

(71) Applicant: PixArt Imaging Inc., Hsin-Chu County (TW)

(72) Inventors: Ren-Hau Gu, Hsin-Chu County (TW); Chih-Hsin Lin, Hsin-Chu County (TW); Yung-Chang Lin, Hsin-Chu County (TW); Chien-Lung Liao, Hsin-Chu County (TW)

(73) Assignee: PIXART IMAGING INC., Hsin-Chu (TW)

( * ) Notice: Subject to any disclaimer, the term of this patent is extended or adjusted under 35 U.S.C. 154(b) by 63 days.

(21) Appl. No.: 16/385,676

(22) Filed: Apr. 16, 2019

(65) Prior Publication Data
US 2019/0239816 A1    Aug. 8, 2019

Related U.S. Application Data

(62) Division of application No. 14/728,051, filed on Jun. 2, 2015, now Pat. No. 10,299,730.

(30) Foreign Application Priority Data

Oct. 29, 2014   (TW) .............................. 103137548 A (51) Int. Cl.
*A61B 5/00* (2006.01)
*A61B 5/024* (2006.01)
*A61B 5/1455* (2006.01)

(52) U.S. Cl.
CPC ............ *A61B 5/7203* (2013.01); *A61B 5/002* (2013.01); *A61B 5/02416* (2013.01); *A61B 5/02438* (2013.01); *A61B 5/14551* (2013.01); *A61B 2560/0271* (2013.01); *A61B 2562/085* (2013.01)

(58) Field of Classification Search
USPC .............................................. 607/4; 600/479
See application file for complete search history.

*Primary Examiner* — Nicole F Lavert
(74) *Attorney, Agent, or Firm* — WPAT, PC (57) ABSTRACT

There is provided a physiological detection system including a physiological detection device and a host. The physiological detection device is configured to transmit a physiological data series to the host according to a local oscillation frequency. The host is configured to calculate a physiological value according to the physiological data series and determine a correction parameter according to a receiving data parameter and a reference data parameter, wherein the correction parameter is configured to correct the physiological value, process the physiological data series or adjust the local oscillation frequency of the physiological detection device.

20 Claims, 5 Drawing Sheets

FIG. 5

HOST OF PHYSIOLOGICAL DETECTION SYSTEM AND PHYSIOLOGICAL DETECTION DEVICE WITH HIGH ACCURACY

RELATED APPLICATIONS

The present application is a divisional application of U.S. application Ser. No. 14/728,051, filed on Jun. 2, 2015, which is based on and claims priority to Taiwanese Application Number 103137548, filed Oct. 29, 2014, the disclosures of which are hereby incorporated by reference herein in their entirety.

BACKGROUND

1. Field of the Disclosure

This disclosure generally relates to a physiological detection system and, more particularly, to a host of a physiological detection system and a physiological detection device with high detection accuracy.

2. Description of the Related Art

A non-invasive physiology detection utilizes a red light beam (wavelength of about 660 nm) and an infrared light beam (wavelength of about 910 nm) to illuminate body tissues, and measures physiological characteristics through detecting a light intensity variation of penetrating light based on that the oxyhemoglobin and the deoxyhemoglobin have different absorptivities for specific light spectrum.

With the popularity of portable electronic devices or wearable electronic devices, the physiological detection function is gradually applied to these electronic devices. Generally, an electronic device employs a crystal oscillator configured as a local oscillator. However, employing a crystal oscillator has a high cost, high circuit complexity and large circuit board size.

SUMMARY

Accordingly, the present disclosure provides a physiological detection system with high accuracy that does not employ a crystal oscillator so as to reduce the cost, simplify the system circuit and decrease the circuit board size.

The present disclosure provides a physiological detection system with high accuracy that includes a physiological detection device employing an adjustable oscillator.

The present disclosure provides a host of a physiological detection system, the host comprising a clock generator and configured to receive a physiological data series sent from a physiological detection device, wherein the physiological data series is sent according to a local oscillation frequency of the physiological detection device, calculate a physiological value according to the physiological data series, calculate a ratio between a reference data parameter, which is a reference accumulation interval or a reference average interval of a host oscillation frequency of the clock generator oscillating for a predetermined oscillating numbers, and a receiving data parameter, which is an accumulation receiving interval or an average receiving interval of the host receiving the predetermined oscillating numbers of physiological data of the physiological data series, to determine a correction parameter, and correct the calculated physiological value according to the correction parameter when the local oscillation frequency of the physiological detection device is different from the host oscillation frequency.

The present disclosure further provides a host of a physiological detection system, the host comprising a clock generator and configured to receive a physiological data series sent from a physiological detection device, wherein the physiological data series is sent according to a local oscillation frequency of the physiological detection device, calculate a ratio between a reference data parameter, which is a reference accumulation interval or a reference average interval of a host oscillation frequency of the clock generator oscillating for a predetermined oscillating numbers, and a receiving data parameter, which is an accumulation receiving interval or an average receiving interval of the host receiving the predetermined oscillating numbers of physiological data of the physiological data series, to determine a correction parameter, process the received physiological data series according to the correction parameter, and calculate a physiological value according to the processed physiological data series to improve accuracy of calculating the physiological value when the local oscillation frequency of the physiological detection device is different from the host oscillation frequency.

The present disclosure further provides a physiological detection device configured to receive a correction parameter from a host, the host comprising a clock generator for providing a host oscillation frequency, send a physiological data series according to a local oscillation frequency of the physiological detection device, and adjust the local oscillation frequency according to the correction parameter when the local oscillation frequency of the physiological detection device is different from the host oscillation frequency, wherein the correction parameter is determined by the host according to a ratio between a reference data parameter, which is a reference accumulation interval or a reference average interval of the host oscillation frequency of the clock generator oscillating for a predetermined oscillating numbers, and a receiving data parameter, which is an accumulation receiving interval or an average receiving interval of the host receiving the predetermined oscillating numbers of physiological data of the physiological data series received from the physiological detection device.

In one embodiment, the reference data parameter is a reference oscillating number of a host oscillation frequency of the host within a predetermined time interval, and the receiving data parameter is a receiving data number of the host receiving physiological data sent from the physiological detection device within the predetermined time interval.

In one embodiment, the correction parameter is associated with a ratio of numbers between the reference oscillating number and the receiving data number.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

Figure 1:
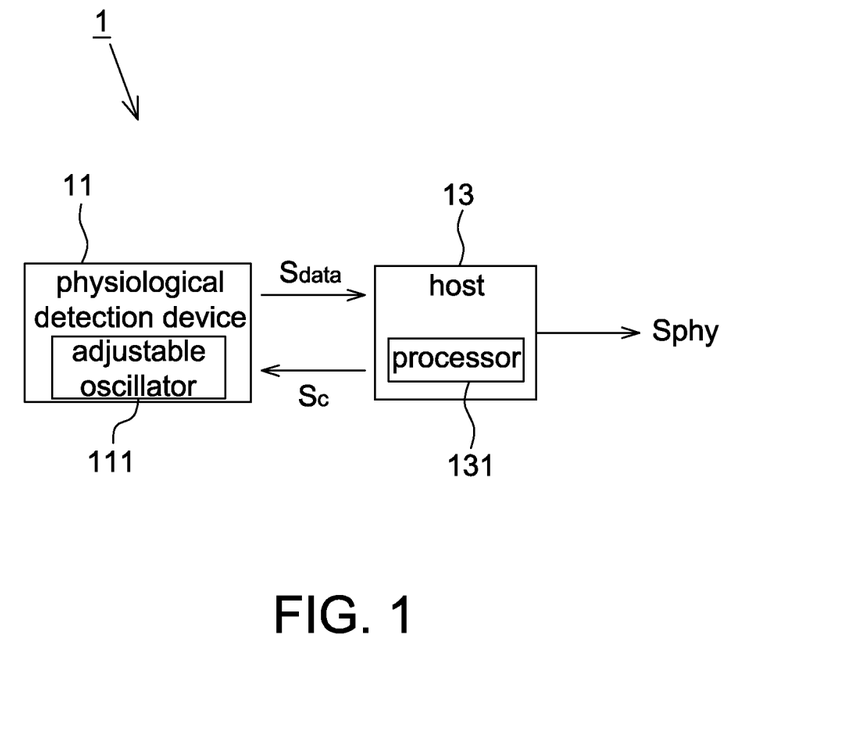
FIG. 1 is a schematic block diagram of a physiological detection system according to one embodiment of the present disclosure.

Referring to FIG. 1, it is a schematic block diagram of a physiological detection system according to one embodiment of the present disclosure. The physiological detection system 1 includes a physiological detection device 11 and a host 13. In one embodiment, the physiological detection device 11 is applicable to a portable electronic device or a wearable electronic device, and is configured to detect physiological data (described later) of a user, wherein the physiological data is, for example, digital data. The physiological detection device 11 also sends a physiological data series $S_{data}$ to the host 13.

The host 13 includes a processor 131 and has a clock generator configured to provide a reference oscillation frequency fb, wherein the processor 131 is, for example, a central processing unit (CPU), a microcontroller (MCU), a microchip or other processors for processing digital data. After receiving the physiological data series $S_{data}$ from the physiological detection device 11 in a wired or wireless manner, the host 11 calculates a physiological value, e.g. a heart rate, according to the physiological data series $S_{data}$, but not limited thereto. In addition, the host 13 further includes a presentation unit, e.g. including a display for showing the physiological value or including a speaker for playing the physiological value, but the present disclosure is not limited thereto as long as the physiological value is presented to the user. In addition, the host 13 further performs other controls according to the physiological value according to different applications.

Figure 2A:
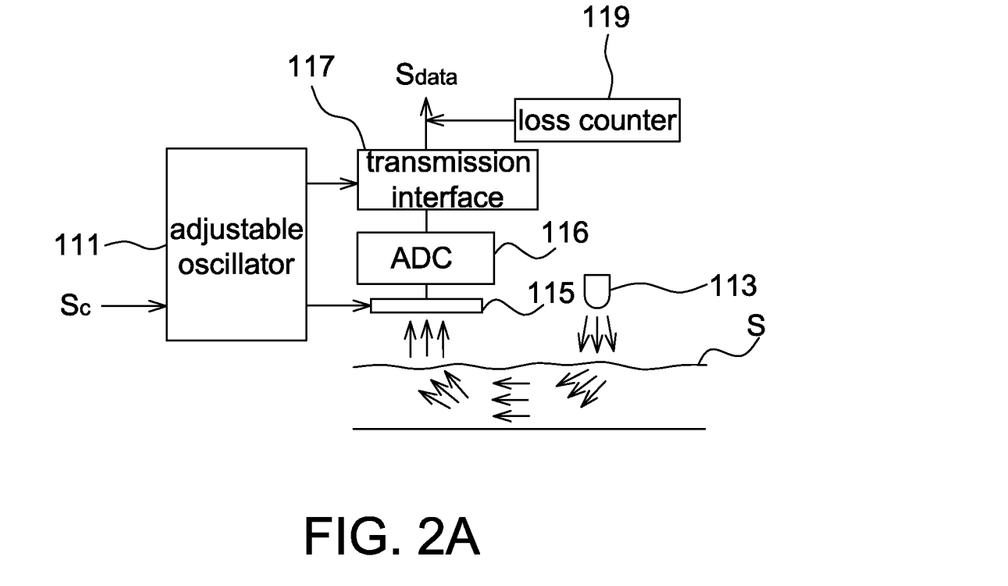
FIGS. 2A-2B are operational schematic diagrams of a physiological detection device according to some embodiments of the present disclosure.
Figure 2B:
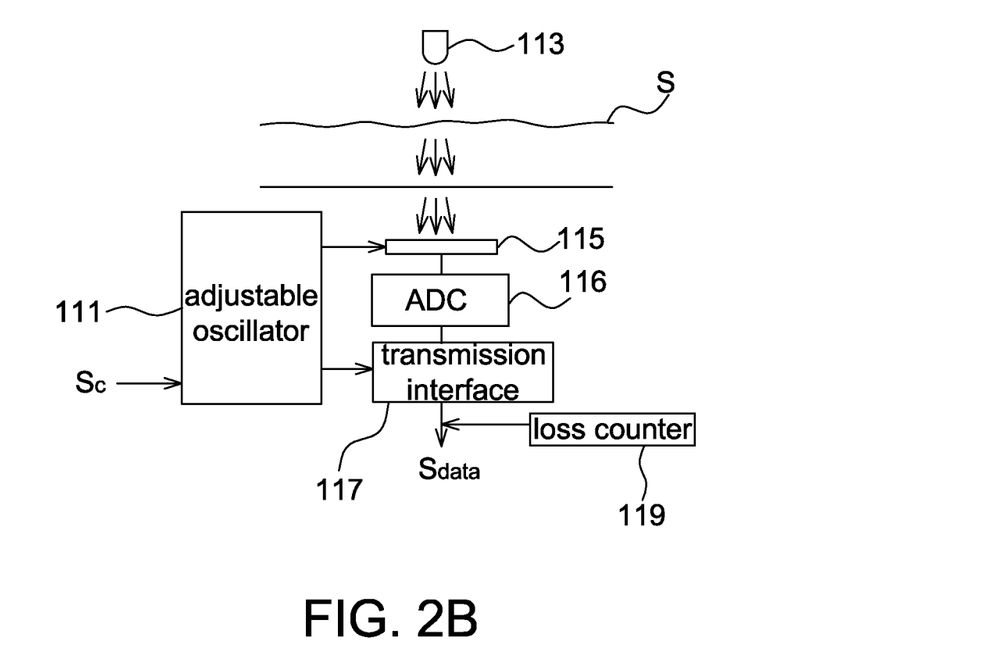

Referring to FIGS. 2A and 2B, they are operational schematic diagrams of a physiological detection device 11 according to some embodiments of the present disclosure. The physiological detection device 11 includes an adjustable oscillator 111, a light source 113, an image sensor 115, an analog-to-digital converter (ADC) 116, a transmission interface 117 and a loss counter 119.

The adjustable oscillator 111 is configured as a local oscillator of the physiological detection device 11, and has a local oscillation frequency f1. To reduce the cost, simplify the system circuit, and decrease the circuit board size, the adjustable oscillator 111 is, for example, an RC oscillator, but not limited thereto.

The light source 113 is configured to emit a light beam suitable to be absorbed by body tissues, e.g. a red light beam (wavelength of about 660 nm) and/or an infrared light beam (wavelength of about 910 nm), to a skin surface S. The light emitted by the light source 113 passes through a part of the body tissues and is then received by the image sensor 115. According to disposed positions of the light sources 113 and the image sensor 115, the physiological detection device 11 is a reflective physiological detection device (as shown in FIG. 2A) or a transmissive physiological detection device (as shown in FIG. 2B). The physiological detection system 1 of the present disclosure is applicable to the physiological detection device 11 of FIGS. 2A and 2B without particular limitations.

The image sensor 115 includes, for example, a complementary metal oxide semiconductor (CMOS) sensor and is configured to sense the light emergent from the body tissues and output detected values (e.g. gray values). According to different applications, the image sensor 115 successively outputs the detected value of every pixel to the ADC 116 to be converted to digital data, or the image sensor 115 adds the detected values of a plurality of pixels at first and then outputs a sum of detected values to the ADC 116 to be converted to digital data.

Figure 3:
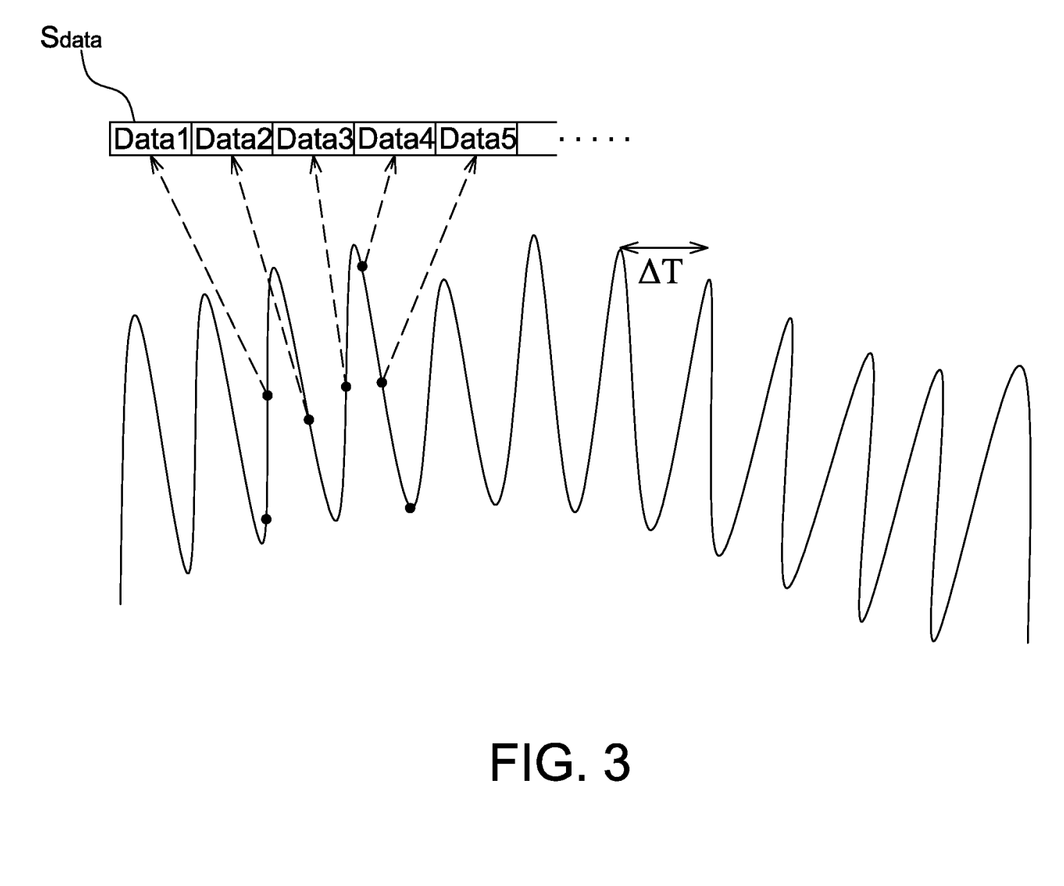
FIG. 3 is a schematic diagram of a physiological data series sent by the physiological detection device according to one embodiment of the present disclosure.

The transmission interface 117 is a wired transmission interface or a wireless transmission interface, and is configured to send, according to the local oscillation frequency f1, a physiological data series $S_{data}$ to the host 13, wherein the wired and wireless transmission techniques are known to the art and thus details thereof are not described herein. For example referring to FIG. 3, it is a schematic diagram of an intensity variation of light emergent through the body tissues. The image sensor 115 performs the sampling according to the local oscillation frequency f1 to obtain detected values, and after the detected values are converted to digital data by the ADC 116, the digital data is sent as a physiological data series $S_{data}$, e.g. Data1 to Data 5 . . . , by the transmission interface 117, i.e. successively sending physiological data. It is appreciated that the density of the physiological data Data1 to Data 5 . . . shown in FIG. 3 is determined according to the local oscillation frequency f1 and is not limited to that shown in FIG. 3.

As mentioned above, as the ADC 116 successively converts the detected value of each pixel or the sum of detected values of a plurality of pixels, each physiological data Data1 to Data 5 . . . of the physiological data series $S_{data}$ is a detected value of a single pixel or a sum of detected values of a plurality of pixels. In another embodiment, the ADC 116 successively converts the detected value of every pixel, and the ADC 116 or the transmission interface 117 further adds the digital data corresponding to a plurality of pixels. In other words, the sum of detected values is a sum of analog signals or a sum of digital data.

Figure 4:
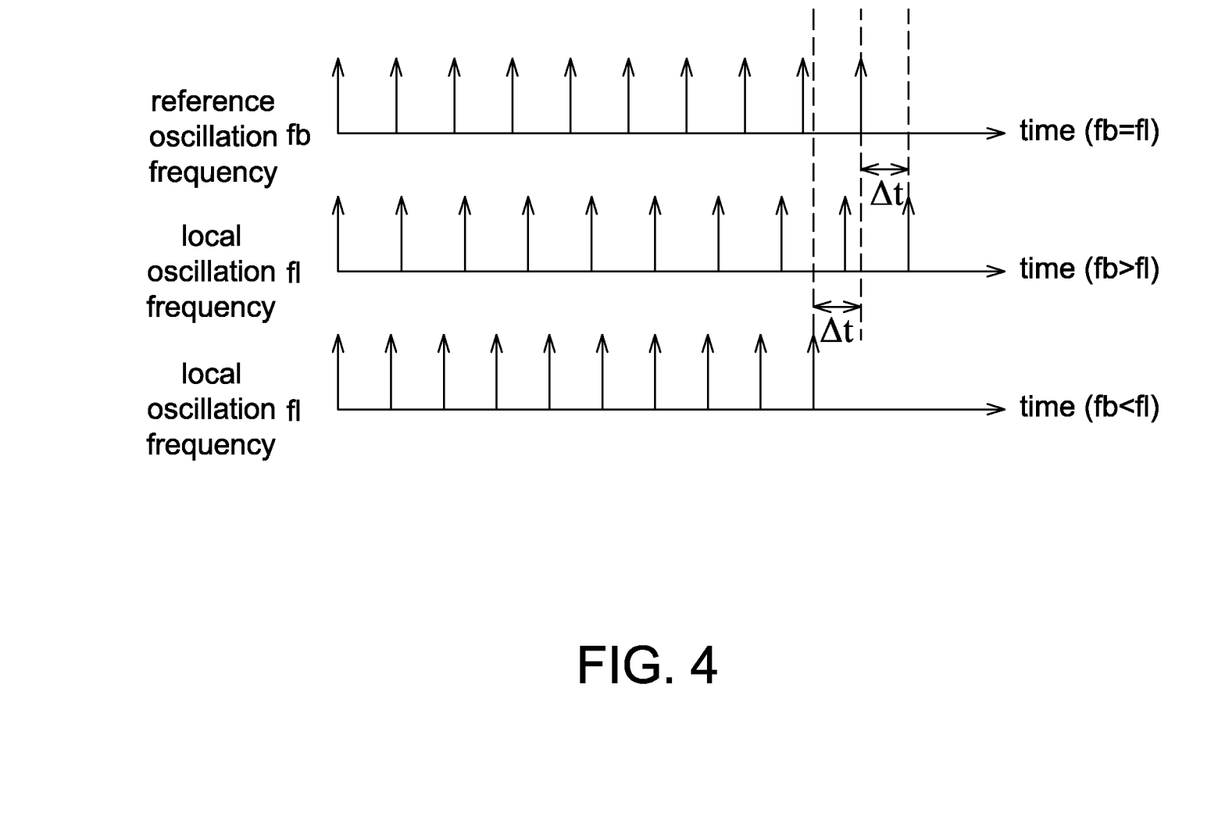
FIG. 4 is a schematic diagram of a reference oscillation frequency of the host and a local oscillation frequency of the physiological detection device in a physiological detection system according to one embodiment of the present disclosure.

As the local oscillation frequency f1 of the adjustable oscillator 111 changes due to the manufacturing process or operating environment, the host 13 may not be able to obtain correct physiological data series $S_{data}$ when the physiological detection device 11 retrieves and sends physiological data according to the local oscillation frequency f1. For example, referring to FIG. 4, it shows that a time shift Δt (or phase shift) between the local oscillation frequency f1 and the reference oscillation frequency fb appears after a time interval when the local oscillation frequency f1 of the physiological detection device 11 is faster or slower than the reference oscillation frequency fb of the host 13. Accordingly, if the local oscillation frequency f1 and the reference oscillation frequency fb are different, errors may be introduced when the host 13 calculates the physiological value according to the physiological data series $S_{data}$ sent from the physiological detection device 11. Therefore, the present disclosure is to solve the problems caused by the mismatch between the oscillation frequencies.

In some conditions, the host 13 losses the physiological data sent from the physiological detection device 11, e.g. when being occupied by other events. Accordingly, in some embodiments, the physiological detection device 11 further includes a loss counter 119 configured to count a data number of the lost physiological data in the physiological data series $S_{data}$ and resend the physiological data next to the physiological data being lost such that the host 13 receives an accurate number of the physiological data. Accordingly, the accuracy of calculating the physiological value is improved.

In a first embodiment, the host 13 is configured to calculate a physiological value according to the physiological data series $S_{data}$, calculate a ratio between a receiving data parameter and a reference data parameter so as to determine a correction parameter Sc, and correct the physiological value according to the correction parameter Sc. In this embodiment, the correction parameter Sc is not transmitted to the physiological detection device 11, or the host 13 transmits the correction parameter Sc to the physiological detection device 11 every a predetermined correction interval, wherein the predetermined correction interval is determined according to the system accuracy.

The host 13 (e.g. the processor 131 thereof) directly calculates a heart rate in the time domain according to the physiological data series $S_{data}$, e.g. calculating a time difference ΔT between adjacent peaks (as shown in FIG. 3) to accordingly derive the heart rate (e.g. calculating a reciprocal of the time different ΔT); or the host 13 converts the physiological data series $S_{data}$ to the frequency domain (e.g. using Fourier Transform, but not limited to) and then calculates the heart rate according to a frequency corresponding to a peak spectrum value.

In one embodiment, the reference data parameter 13 is a reference oscillating number of a host oscillation frequency of the host 13 oscillating for a predetermined time interval. For example referring to Table 1, when a host oscillation frequency is 1000 times/second and the predetermined time interval is 1 second, the reference oscillating number is 1000 times.

In this embodiment, the receiving data parameter is a receiving data number of the host 13 (e.g. each of Data1 to Data 5 shown in FIG. 3 indicating one receiving data) for receiving the physiological data series $S_{data}$ from the physiological detection device 11 within the predetermined time interval. For example referring to Table 1 again, when a local oscillation frequency f1 of the physiological detection device 11 is 1100 times/second, a receiving data number of the host 13 for receiving the physiological data series $S_{data}$ from the physiological detection device 11 within the predetermined time interval (e.g. 1 second) is 1100 times; and when the local oscillation frequency f1 of the physiological detection device 11 is 900 times/second, a receiving data number of the host 13 for receiving the physiological data series $S_{data}$ from the physiological detection device 11 within the predetermined time interval (e.g. 1 second) is 900 times.

In this embodiment, the correction parameter Sc is associated with a ratio of numbers between the reference oscillating number and the receiving data number, e.g. 11/10, 9/10 shown in Table 1. For example, the correction parameter Sc is equal to the ratio of numbers or is a multiple of, a fraction of or a shift from the ratio of numbers. In some embodiments, the host oscillation frequency is a multiple or a fraction of an operating frequency of the host 13.

TABLE 1

| reference oscillating number | 1000 times | 1000 times |
| receiving data number | 1100 times | 900 times |
| correction parameter Sc | 11/10 | 9/10 |

In another embodiment, the reference data parameter is a reference accumulation interval or a reference average interval of a host oscillation frequency of the host 13 oscillating for a predetermined oscillating numbers. For example referring to Table 2, when a host oscillation frequency is 1000 times/second and the predetermined oscillating numbers is 1000 times, the reference accumulation interval is 1 second and the reference average interval is 0.001 second.

In this embodiment, the receiving data parameter is an accumulation receiving interval or an average receiving interval of the host 13 for receiving the predetermined oscillating numbers of physiological data of the physiological data series $S_{data}$ sent from the physiological detection device 11. For example referring to Table 2, when a local oscillation frequency f1 of the physiological detection device 11 is 1100 times/second, an accumulation receiving interval of the host 13 for receiving the predetermined oscillating numbers (e.g. 1000 times) of physiological data of the physiological data series $S_{data}$ is 1.1 second and the average receiving interval is 0.0011 second; when the local oscillation frequency f1 of the physiological detection device 11 is 900 times/second, an accumulation receiving interval of the host 13 for receiving the predetermined oscillating numbers (e.g. 1000 times) of physiological data of the physiological data series $S_{data}$ is 0.9 second and the average receiving interval is 0.0009 second.

In this embodiment, the correction parameter Sc is associated with a ratio of intervals between the reference accumulation interval and the accumulation receiving interval, or associated with a ratio of intervals between the reference average interval and the average receiving interval, e.g. 10/11, 10/9 shown in Table 2. For example, the correction parameter Sc is equal to the ratio of intervals or is a multiple of, a fraction of or a shift from the ratio of intervals.

TABLE 2

| reference accumulation interval | 1 second | 1 second |
| accumulation receiving interval | 1.1 second | 0.9 second |
| correction parameter Sc | 10/11 | 10/9 |

In a second embodiment, the host 13 is configured to calculate a ratio between a receiving data parameter and a reference data parameter so as to determine a correction parameter Sc, to process the physiological data series $S_{data}$ according to the correction parameter Sc, and calculate a physiological value according to the processed physiological data series. In this embodiment, definitions of the receiving data parameter, the reference data parameter and the correction parameter are identical to those of the first embodiment, as shown in Tables 3 and 4, and thus details thereof are not repeated herein. Similarly, in this embodiment the correction parameter Sc is not transmitted to the physiological detection device 11, or the host 13 transmits the correction parameter Sc to the physiological detection device 11 every a predetermined correction interval, wherein the predetermined correction interval is determined according to the system accuracy.

The difference between the second embodiment and the first embodiment is that in the second embodiment the host 13 (e.g. the processor 131 thereof) is configured to process the physiological data series $S_{data}$ according to the correction parameter Sc.

In one embodiment, when the reference oscillating number is smaller than the receiving data number, the host 13 is configured to perform downsampling on the physiological data series $S_{data}$ such that a data number of the processed physiological data series is equal to the reference oscillating number. For example referring to Table 3, when a reference oscillating number is 1000 times and a receiving data number is 1100 times, the correction parameter Sc is a multiple of, a fraction of or a shift from 11/10. The host 13 performs the downsampling according to the correction parameter Sc. The host 13 (e.g. the processor 131 thereof) calculates a physiological value according to the processed physiological data series, wherein the method of calculating the physiological value is illustrated in the first embodiment and thus details thereof are not repeated herein.

In this embodiment, when the reference oscillating number is larger than the receiving data number, the host 13 is configured to perform interpolation on the physiological data series $S_{data}$ such that a data number of the processed physiological data series is equal to the reference oscillating number. For example referring to Table 3 again, when a reference oscillating number is 1000 times and a receiving data number is 900 times, the correction parameter Sc is a multiple of, a fraction of or a shift from 9/10. The host 13 performs the interpolation according to the correction parameter Sc. The host 13 (e.g. the processor 131 thereof) calculates a physiological value according to the processed physiological data series, wherein the method of calculating the physiological value is illustrated in the first embodiment and thus details thereof are not repeated herein. In some embodiments, the host oscillation frequency is a multiple or a fraction of an operating frequency of the host 13.

TABLE 3

| reference oscillating number | 1000 times | 1000 times |
|---|---|---|
| receiving data number | 1100 times | 900 times |
| correction parameter Sc | 11/10 | 9/10 |
| processing physiological data series | downsampling | interpolation |

In another embodiment, when the accumulation receiving interval is smaller than the reference accumulation interval or when the average receiving interval is smaller than the reference average interval, the host 13 is configured to perform downsampling on the physiological data series $S_{data}$ such that a data number of the processed physiological data series is equal to the reference oscillating number. For example referring to Table 4, when a reference accumulation interval is 1 second (or the reference average interval is 0.001 second) and an accumulation receiving interval is 0.9 second (or the average receiving interval is 0.0009 second), the correction parameter Sc is a multiple of, a fraction of or a shift from 10/9. The host 13 performs the downsampling according to the correction parameter Sc. The host 13 (e.g. the processor 131 thereof) calculates a physiological value according to the processed physiological data series, wherein the method of calculating the physiological value is illustrated in the first embodiment and thus details thereof are not repeated herein.

In this embodiment, when the accumulation receiving interval is larger than the reference accumulation interval or when the average receiving interval is larger than the reference average interval, the host 13 is configured to perform interpolation on the physiological data series $S_{data}$ such that a data number of the processed physiological data series is equal to the reference oscillating number. For example referring to Table 4 again, when a reference accumulation interval is 1 second (or the reference average interval is 0.001 second) and an accumulation receiving interval is 1.1 second (or the average receiving interval is 0.0011 second), the correction parameter Sc is a multiple of, a fraction of or a shift from 10/11. The host 13 performs the interpolation according to the correction parameter Sc. The host 13 (e.g. the processor 131 thereof) calculates a physiological value according to the processed physiological data series, wherein the method of calculating the physiological value is illustrated in the first embodiment and thus details thereof are not repeated herein.

TABLE 4

| reference accumulation interval | 1 second | 1 second |
|---|---|---|
| accumulation receiving interval | 1.1 second | 0.9 second |
| correction parameter Sc | 10/11 | 10/9 |
| processing physiological data series | interpolation | downsampling |

In a third embodiment, the host 13 is configured to calculate a ratio between a receiving data parameter and a reference data parameter so as to determine a correction parameter Sc, to transmit the correction parameter Sc to the physiological detection device 11, and to calculate a heart rate according to the physiological detection series $S_{data}$, wherein the physiological detection device 11 is further configured to adjust the local oscillation frequency f1 thereof according to the correction parameter Sc. In this embodiment, definitions of the receiving parameter, the reference data parameter and the correction parameter are identical to those of the first embodiment, as shown in Tables 5 and 6, and thus details thereof are not repeated herein.

The difference between the third embodiment and the first and second embodiments is that in the third embodiment the host 13 transmits the correction parameter Sc to the physiological detection device 11, and the physiological detection device 11 adjusts the local oscillation frequency f1 of the adjustable oscillator 111 thereof according to the correction parameter Sc.

In one embodiment, when the reference oscillating number (e.g. 1000 times) is smaller than the receiving data number (e.g. 1100 times), it means that the local oscillation frequency f1 is too high and thus the host 13 transmits the correction parameter Sc to the physiological detection device 11 and the adjustable oscillator 111 decreases the local oscillation frequency f1 to close to the reference oscillation frequency fb according to the correction parameter Sc; and when the reference oscillating number (e.g. 1000 times) is larger than the receiving data number (e.g. 900 times), it means that the local oscillation frequency f1 is too low and thus the host 13 transmits the correction parameter Sc to the physiological detection device 11 and the adjustable oscillator 111 increases the local oscillation frequency f1 to close to the reference oscillation frequency fb according to the correction parameter Sc. In some embodiment, the host oscillation frequency is a multiple or a fraction of an operating frequency of the host 13.

TABLE 5

| reference oscillating number | 1000 times | 1000 times |
|---|---|---|
| receiving data number | 1100 times | 900 times |
| correction parameter Sc | 10/11 | 10/9 |

In another embodiment, when the accumulation receiving interval (e.g. 0.9 second) is smaller than the reference accumulation interval (e.g. 1 second), it means that the local oscillation frequency f1 is too high and thus the host 13 transmits the correction parameter Sc to the physiological detection device 11 and the adjustable oscillator 111 decreases the local oscillation frequency f1 to close to the reference oscillation frequency fb according to the correction parameter Sc; and when the accumulation receiving interval (e.g. 1.1 second) is larger than the reference accumulation interval (e.g. 1 second), it means that the local oscillation frequency f1 is too low and thus the host 13 transmits the correction parameter Sc to the physiological detection device 11 and the adjustable oscillator 111 increases the local oscillation frequency f1 to close to the reference oscillation frequency fb according to the correction parameter Sc.

TABLE 6

| reference accumulation interval | 1 second | 1 second |
| accumulation receiving interval | 1.1 second | 0.9 second |
| correction parameter Sc | 11/10 | 9/10 |

It is appreciated that the host 13 further includes a transmission interface configured to receive the physiological data and transmit the correction parameter. In addition, values in the above embodiments are only intended to illustrate but not to limit the present disclosure.

Figure 5:
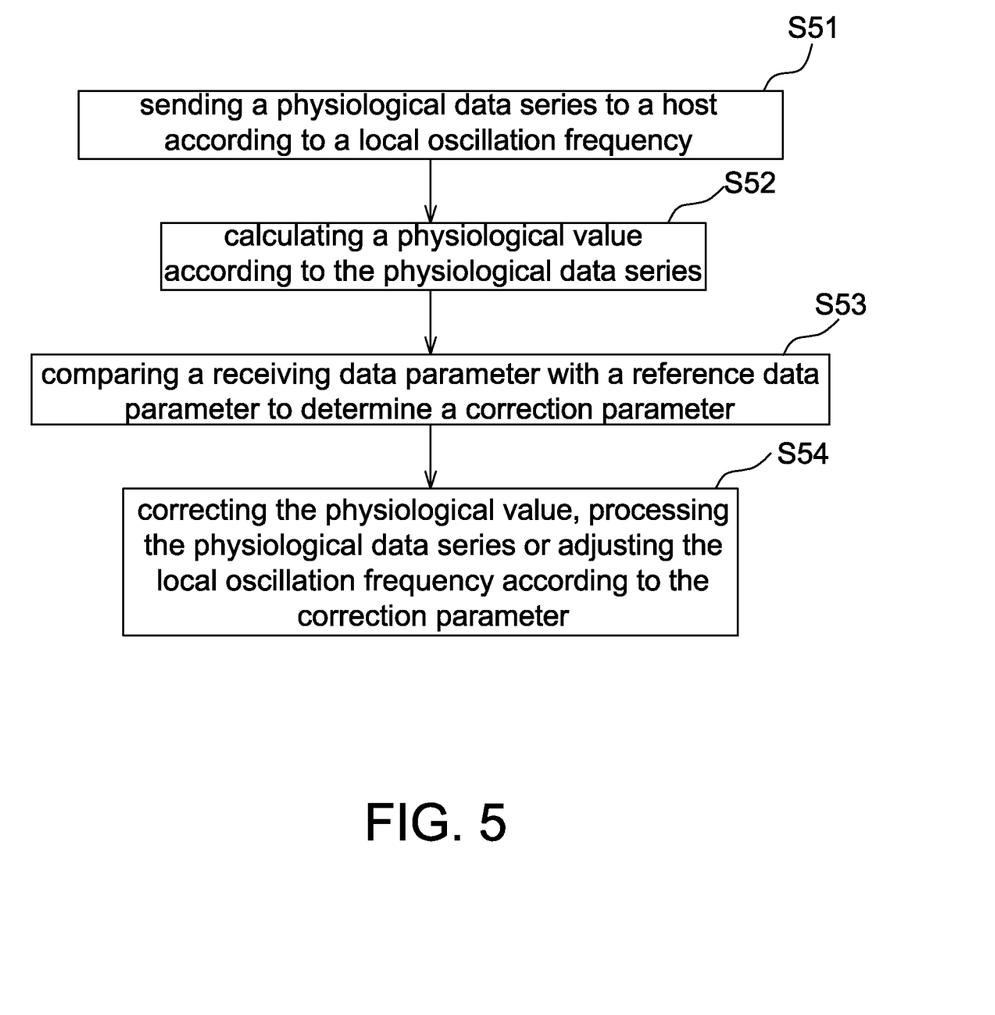
FIG. 5 is a flow chart of a correction method of a physiological detection system according to one embodiment of the present disclosure.

Referring to FIG. 5, it is a flow chart of a correction method of a physiological detection system according to one embodiment of the present disclosure, which includes the steps of: sending a physiological data series to a host according to a local oscillation frequency (Step S51); calculating a physiological value according to the physiological data series (Step S52); comparing a receiving data parameter with a reference data parameter to determine a correction parameter (Step S53); and correcting the physiological value, processing the physiological data series or adjusting the local oscillation frequency according to the correction parameter (Step S54). Referring to FIGS. 1-5 together, details of this embodiment are illustrated hereinafter.

Step S51: The physiological detection device 11 detects physiological data according to a local oscillation frequency f1 thereof and sends, through a transmission interface 117 thereof, a physiological data series $S_{data}$ to the host 13 according to the local oscillation frequency f1 in a wired or wireless manner.

Step S52: After receiving the physiological data series $S_{data}$, the host 13 calculates a physiological value, e.g. a heart rate, in the time domain or frequency domain according to the physiological data series $S_{data}$. In this case, the heart rate is possible to be corrected in the following steps.

Step S53: After receiving the physiological data series $S_{data}$, the host 13 further compares a receiving data parameter with a reference data parameter so as to determine a correction parameter Sc, as illustrated in the above first to third embodiments. For example, the host 13 determines whether to perform the correction according to whether the correction parameter Sc exceeds a predetermined range, wherein the predetermined range is determined according to the system accuracy.

Step S54: According to different embodiments, the host 13 performs different processing so as to improve the accuracy of calculating the physiological value. For example, in the first embodiment the host 13 directly corrects the physiological value according to the correction parameter Sc such that even though the local oscillation frequency f1 of the physiological detection device 11 is not correct, the host 13 is still able to output correct physiological values. In the second embodiment, the host 13 processes the physiological data series $S_{data}$ according to the correction parameter Sc, e.g. downsampling or interpolation, such that even though the local oscillation frequency f1 of the physiological detection device 11 is not correct, the host 13 is still able to output correct physiological values. In the third embodiment, the host 13 transmits the correction parameter Sc back to the physiological detection device 11 for the physiological detection device 11 to accordingly adjust the local oscillation frequency f1 thereof such that the physiological value calculated according to the local oscillation frequency f1 before being corrected is not outputted. After the local oscillation frequency f1 is corrected, the host 13 outputs the physiological value calculated according the corrected physiological data series.

It is appreciated that the calculation of the host 13 is executed by the processor by means of software or hardware.

As mentioned above, the conventional electronic device employing a crystal oscillator has a high cost, complex system circuit and large circuit board size. Therefore, the present disclosure further provides a physiological detection system with high accuracy (FIG. 1) which employs an adjustable oscillator to replace the crystal oscillator and determines a correction parameter through comparing a receiving data parameter and a reference data parameter to accordingly correct a physiological value.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A host of a physiological detection system, the host comprising a clock generator and configured to
   receive a physiological data series sent from a physiological detection device, wherein the physiological data series is sent according to a local oscillation frequency of the physiological detection device,
   calculate a physiological value according to the physiological data series,
   calculate a ratio between a reference data parameter, which is a reference accumulation interval or a reference average interval of a host oscillation frequency of the clock generator oscillating for a predetermined oscillating numbers, and a receiving data parameter, which is an accumulation receiving interval or an average receiving interval of the host receiving the predetermined oscillating numbers of physiological data of the physiological data series, to determine a correction parameter, and
   correct the calculated physiological value according to the correction parameter when the local oscillation frequency of the physiological detection device is different from the host oscillation frequency.

2. The host as claimed in claim 1, wherein the physiological value is a heart rate.

3. The host as claimed in claim 1, wherein the correction parameter is associated with a ratio of the reference accumulation interval and the accumulation receiving interval, or a ratio of the reference average interval and the average receiving interval.

4. The host as claimed in claim 1, wherein the host is configured to transmit the correction parameter every predetermined correction interval.

5. The host as claimed in claim 4, wherein the transmitted correction parameter is configured to adjust the local oscillation frequency of an adjustable oscillator of the physiological detection device.

6. The host as claimed in claim 1, wherein each physiological data of the physiological data series is a detected value of a single pixel or a sum of detected values of a plurality of pixels of a CMOS sensor.

7. The host as claimed in claim 1, wherein the physiological detection device further comprises a loss counter configured to count a data number of lost physiological data of the physiological data series.

8. A host of a physiological detection system, the host comprising a clock generator and configured to
receive a physiological data series sent from a physiological detection device, wherein the physiological data series is sent according to a local oscillation frequency of the physiological detection device,
calculate a ratio between a reference data parameter, which is a reference accumulation interval or a reference average interval of a host oscillation frequency of the clock generator oscillating for a predetermined oscillating numbers, and a receiving data parameter, which is an accumulation receiving interval or an average receiving interval of the host receiving the predetermined oscillating numbers of physiological data of the physiological data series, to determine a correction parameter,
process the received physiological data series according to the correction parameter, and
calculate a physiological value according to the processed physiological data series to improve accuracy of calculating the physiological value when the local oscillation frequency of the physiological detection device is different from the host oscillation frequency.

9. The host as claimed in claim 8, wherein the physiological value is a heart rate.

10. The host as claimed in claim 8, wherein the correction parameter is associated with a ratio of the reference accumulation interval and the accumulation receiving interval, or a ratio of the reference average interval and the average receiving interval.

11. The host as claimed in claim 10, wherein the host is configured to perform downsampling on the physiological data series when the accumulation receiving interval is smaller than the reference accumulation interval or when the average receiving interval is smaller than the reference average interval.

12. The host as claimed in claim 10, wherein the host is configured to perform interpolation on the physiological data series when the accumulation receiving interval is larger than the reference accumulation interval or when the average receiving interval is larger than the reference average interval.

13. The host as claimed in claim 8, wherein the host is configured to transmit the correction parameter every predetermined correction interval.

14. The host as claimed in claim 13, wherein the transmitted correction parameter is configured to adjust the local oscillation frequency of an adjustable oscillator of the physiological detection device.

15. The host as claimed in claim 8, wherein each physiological data of the physiological data series is a detected value of a single pixel or a sum of detected values of a plurality of pixels of a CMOS sensor.

16. The host as claimed in claim 8, wherein the physiological detection device further comprises a loss counter configured to count a data number of lost physiological data of the physiological data series.

17. A physiological detection device, the physiological detection device configured to
receive a correction parameter from a host, the host comprising a clock generator for providing a host oscillation frequency,
send a physiological data series according to a local oscillation frequency of the physiological detection device, and
adjust the local oscillation frequency according to the correction parameter when the local oscillation frequency of the physiological detection device is different from the host oscillation frequency,
wherein the correction parameter is determined by the host according to a ratio between a reference data parameter, which is a reference accumulation interval or a reference average interval of the host oscillation frequency of the clock generator oscillating for a predetermined oscillating numbers, and a receiving data parameter, which is an accumulation receiving interval or an average receiving interval of the host receiving the predetermined oscillating numbers of physiological data of the physiological data series received from the physiological detection device.

18. The physiological detection device as claimed in claim 17, wherein the correction parameter is associated with a ratio of the reference accumulation interval and the accumulation receiving interval, or a ratio of the reference average interval and the average receiving interval.

19. The physiological detection device as claimed in claim 17, wherein the physiological detection device further comprises a loss counter configured to count a data number of lost physiological data of the physiological data series.

20. The physiological detection device as claimed in claim 17, wherein the physiological detection device further comprises a CMOS sensor, and each physiological data of the physiological data series is a detected value of a single pixel or a sum of detected values of a plurality of pixels of the CMOS sensor.

* * * * *